United States Patent

Puvvada et al.

[11] Patent Number: 5,952,286
[45] Date of Patent: Sep. 14, 1999

[54] LIQUID CLEANSING COMPOSITION COMPRISING SOLUBLE, LAMELLAR PHASE INDUCING STRUCTURANT AND METHOD THEREOF

[75] Inventors: Sudhakar Puvvada, Hackensack; Virgilio Villa, Bergenfield; Richard Kolodziej, Cliffside Park, all of N.J.

[73] Assignee: Lever Brothers Company, New York, N.Y.

[21] Appl. No.: 08/789,726

[22] Filed: Jan. 27, 1997

Related U.S. Application Data

[63] Continuation of application No. 08/512,010, Aug. 7, 1995, abandoned.

[51] Int. Cl.⁶ .............................. F11D 17/00; B08B 7/00
[52] U.S. Cl. ..................... 510/417; 510/130; 510/424; 510/428; 510/463; 510/466; 424/70.1; 134/40
[58] Field of Search ................... 510/130, 131, 510/122, 125, 123, 463, 124, 424, 417, 422, 426, 403, 428, 466; 424/70, 489, 562, 846, 70.1; 134/40

[56] References Cited

U.S. PATENT DOCUMENTS

| | | | |
|---|---|---|---|
| 3,829,560 | 8/1974 | Barry et al. | 424/70 |
| 4,883,659 | 11/1989 | Goulman et al. | 424/78 |
| 5,015,471 | 5/1991 | Birtwistle et al. | 424/70 |
| 5,132,037 | 7/1992 | Greene et al. | 252/108 |
| 5,158,699 | 10/1992 | MacGlip et al. | 252/108 |
| 5,234,619 | 8/1993 | Greene et al. | 252/108 |
| 5,290,471 | 3/1994 | Greene et al. | 252/108 |
| 5,296,157 | 3/1994 | MacGlip et al. | 252/108 |
| 5,308,526 | 5/1994 | Dias et al. | 252/125 |
| 5,360,581 | 11/1994 | Rizvi et al. | 252/544 |
| 5,540,853 | 7/1996 | Trinh et al. | 510/101 |
| 5,543,074 | 8/1996 | Hague et al. | 510/122 |
| 5,612,307 | 3/1997 | Chambers et al. | 510/406 |
| 5,632,978 | 5/1997 | Moore et al. | 510/159 |

FOREIGN PATENT DOCUMENTS

| | | |
|---|---|---|
| 94/15666 | 9/1992 | WIPO . |
| 93/18737 | 9/1993 | WIPO . |
| 94/01084 | 1/1994 | WIPO . |
| 94/ 17166 | 8/1994 | WIPO . |

OTHER PUBLICATIONS

Copending application: U.S. S/N 08/469,949—Shana'a—Filed Jun. 6, 1995.

*Primary Examiner*—Necholus Ogden
*Attorney, Agent, or Firm*—Ronald A. Koatz

[57] ABSTRACT

The present invention relates to lamellar phase compositions comprising defined surfactant systems and a structurant selected from the group consisting of liquid fatty acids liquid alcohols and derivatives thereof which structurant is responsible for inducing the lamellar phrase. The invention also relates to a method of inducing said lamellar phase in such compositions by adding the defined structurant.

5 Claims, No Drawings

LIQUID CLEANSING COMPOSITION COMPRISING SOLUBLE, LAMELLAR PHASE INDUCING STRUCTURANT AND METHOD THEREOF

This is a Continuation application of Ser. No. 08/512,010, filed Aug. 7, 1995 now abandoned.

BACKGROUND

Field of the Invention

The present invention relates to liquid cleansing compositions of the type which are typically used as skin cleansing or shower gel compositions. In particular, the invention relates to lamellar phase compositions which are readily shear thinning (i.e., can suspend large particles, such as 1 micron and larger, because of their high zero shear viscosity; and yet still readily pour). In addition, the product also "heaps" on dispensing and is soft and lotion-like, thereby providing consumers a signal of enhanced moisturization.

BACKGROUND OF THE INVENTION

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning).

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. Again, however, they are generally more expensive to make (e.g., they are restricted as to which surfactants can be used and often require greater concentration of surfactants).

Unexpectedly, applicants have now found that if certain liquid fatty acids (e.g., long chain, unsaturated and/or branched fatty acids); long chain, unsaturated and/or branched alcohols (e.g., oleyl alcohol or isostearyl alcohol) or derivatives (ester of fatty acids and ether of fatty alcohols) of these fatty acids and/or alcohols are used in a typical rod-micellar solution, a lamellar phase can be induced.

Specifically, applicants have found that, in compositions comprising (1) one or more anionic surfactants; (2) at least one amphoteric and/or zwitterionic surfactant; and (3) optionally, one or more nonionic surfactants; when a liquid structurant as noted above (i.e., long chain, unsaturated and/or branched liquid fatty acid; long chain unsaturated and/or branched liquid alcohols or derivatives thereof) having a melting point below about 25° C. is added, the compositions become lamellar phase compositions. Further, with these specific structurants, there is no crystallization of the structurant.

The use of fatty acids generally in liquid cleansers (shower gels and shampoos) is taught, for example, in WO 94/17166 to Giret et al. (assigned to Procter & Gamble); WO 94/18737 to Cothran et al. (assigned to Procter & Gamble) and in U.S. Pat. Nos. 5,132,037; 5,234,619; and 5,290,470; each to Greene et al.

Each of these references, however, teach the use of linear, saturated fatty acids (versus the unsaturated or branched fatty acids of the subject invention) which are insoluble and which crystalize in the products. Indeed, in these references, it is intended to crystallize the fatty acids since this is an important factor in the structuring, (see WO 93/18737 at page 5, lines 23–32). These references also do not teach unsaturated or branched, long chain alcohols or their ether derivatives.

Dias et al. (WO 94/01084, U.S. Pat. No. 5,308,526), MacGilp et al. (U.S. Pat. Nos. 5,158,699; 5,296,157; WO 92/15666) and Torres (WO 94/01085) teach the use of free fatty acids and potassium fatty acid soap where said fatty acid has an Iodine Value between 0 to 15 (i.e., iodine values indicate level of saturation of the fatty acids). In addition, there is no teaching of unsaturated or branched, long chain fatty acid or alcohol.

U.S. Pat. No. 5,360,581 to Rizvi et al. teach the use of a long chained saturated fatty acid (preferably $C_{22}$) with polyethyleneimine to increase stability of the product. The fatty acid is saturated compared to the liquid, unsaturated fatty acid of the subject invention.

Japanese patent JP 7,025,726 teaches the use of liquid fatty acids in emulsion. The patent teaches compositions having 30% or greater oil by which is meant an emollient (e.g., vegetable oil) while the compositions of the subject invention comprise no more than about 20%, preferably no more than about 15% by wt. oil/emollient. Furthermore, JP 7,025,726 does not teach the use of liquid fatty acid as a structurant while the present invention utilizes the liquid fatty acid to generate the lamellar phase and thus structures the product.

Finally, applicants' copending application Ser. No. 08/469,949 to Shana'a relates to soap composition which comprises 5 to 35% $C_8$ to $C_{22}$ fatty acid of which 20–50% must be un-neutralized (i.e., more than 50% is neutralized to form soap). The present application is a soap-free application and such compositions are generally milder. Moreover, it would not have been obvious that addition of the structurants of the subject invention in the absence of soap would yield lamellar phase compositions.

BRIEF SUMMARY OF THE INVENTION

The present invention relates to a liquid cleansing composition comprising a surfactant system (comprising, e.g., anionic or anionics plus amphoteric/zwitterionic), and 0.1 to 15%, preferably 0.5 to 10% by weight of a lamellar phase inducing structurant wherein said structurant is selected from the group consisting of unsaturated and/or branched, long chain (i.e., $C_8$ to $C_{24}$, preferably $C_{12}$ to $C_{24}$) liquid fatty acids or ester derivatives of these fatty acids; unsaturated and/or branched, long chain (i.e., $C_8$ to $C_{24}$, preferably $C_{12}$ to $C_{24}$) liquid alcohols or ether derivatives of these alcohols.

Short chain, saturated, fatty acids ($C_5$ to $C_9$ liquid fatty acids or derivatives) can also be used though these are not preferred.

In a second embodiment of the invention, the invention relates to a method of inducing the formation of a lamellar phase liquid cleaning composition comprising the surfactant system described above which method comprises adding to the composition about 0.1 to 15%, preferably 0.5 to 10% by weight of a structurant as defined above and having a melting point (MP) below about 25° C.

DETAILED DESCRIPTION OF THE INVENTION

The present invention relates to liquid cleansing compositions comprising specified surfactant systems and wherein a structurant is used to induce a phase change to lamellar phase composition. Such lamellar phase compositions are preferred because they can readily suspend particles such as emollient particles (i.e., due to high zero shear viscosity) and yet readily pour out (i.e., are highly shear thinning). In addition, use of these structurants allows less surfactant to be used and provides greater versatility (i.e., can be used in many more surfactant systems of which applicants are aware) than previously possible. Further, the lamellar compositions are soft and "heap" upon dispensing thus providing a desirable and consumer pleasing rheology. The compositions are set forth in greater detail below.

Surfactants

The surfactant system of the subject invention comprises 5 to 50% by weight, preferably 10 to 40% by wt. of the composition and comprises:

(a) one or more anionic surfactants;

(b) amphoteric and/or zwitterionic surfactant; and (c) optional nonionic surfactant The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula

$$R^4CONHCH_2CH_2O_2CCH_2CH(SO_3M)CO_2M$$

wherein $R^4$ ranges from $C_8$–$C_{22}$ alkyl and M is a solubilizing cation;

amido-MIPA sulfosuccinates of formula

$$RCONH(CH_2)CH(CH_3)(SO_3M)CO_2M$$

where M is as defined above.

Also included are the alkoxylated citrate sulfosuccinates; and alkoxylated sulfosuccinates such as the following:

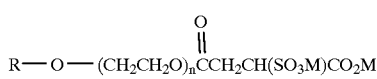

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula

$$RCON(CH_3)CH_2CO_2M,$$

wherein R ranges from $C_8$ to $C_{20}$ alkyl and M is a solubilizing cation.

Taurates are generally identified by formula

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ$^{(R)}$ by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

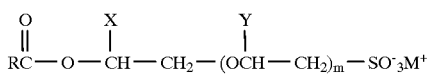
$$\underset{}{\overset{O}{\underset{\|}{RC}}}-O-\underset{}{\overset{X}{\underset{|}{CH}}}-CH_2-(O\underset{}{\overset{Y}{\underset{|}{CH}}}-CH_2)_m-SO_3^-M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

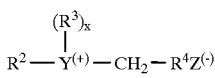
$$R^2-\underset{\underset{}{}}{\overset{(R^3)_x}{\underset{|}{Y^{(+)}}}}-CH_2-R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

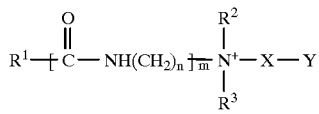
$$R^1-\underset{}{\overset{O}{\underset{\|}{C}}}-NH(CH_2)_n\overline{\phantom{|}}_m\underset{\underset{R^3}{|}}{\overset{R^2}{\underset{|}{N^+}}}-X-Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Suitable amphoteric detergents within the above general formula include simple betaines of formula:

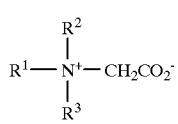
$$R^1-\underset{\underset{R^3}{|}}{\overset{R^2}{\underset{|}{N^+}}}-CH_2CO_2^-$$

and amido betaines of formula:

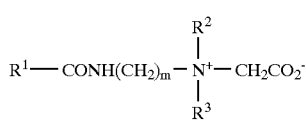
$$R^1-CONH(CH_2)_m-\underset{\underset{R^3}{|}}{\overset{R^2}{\underset{|}{N^+}}}-CH_2CO_2^-$$

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

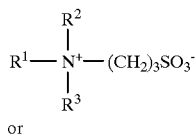

or

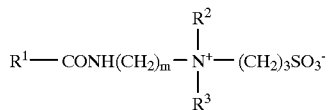

where m is 2 or 3, or variants of these in which —$(CH_2)_3SO_3$— is replaced by

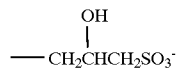

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic generally comprises 0.1 to 20% by weight, preferably 5% to 15% of the composition.

In addition to one or more anionic and amphoteric and/or zwitterionic, the surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

In general, the compositions of the invention are soap-free compositions. The generation of lamellar phase in such soap-free composition was completely unexpected.

Structurant

The present invention provides compositions utilizing about 0.1% to 15% by wt., preferably 1 to 10% by wt. of a structuring agent which works in the compositions to form a lamellar phase. Such lamellar phase is preferred because it enables the compositions to suspend particles more readily (e.g., emollient particles) while still maintaining good shear thinning properties. The lamellar phase also provides consumers with desired rheology ("heaping").

More particularly, where the composition is not lamellar structured and enhanced particle suspension/enhancing is desired, it is usually necessary to add external structurants such as carbomers (e.g., cross-linked polyacrylate such as Carbopol$^{(R)}$) and clays. However, these external structurants have poorer shear thinning properties that significantly reduce consumer acceptability.

The structurant is generally an unsaturated and/or branched long chain ($C_8$–$C_{24}$) liquid fatty acid or ester derivative thereof; and/or unsaturated and/or branched long chain liquid alcohol or ether derivatives thereof. It may also be a short chain saturated fatty acid such as capric acid or caprylic acid. While not wishing to be bound by theory, it is believed that the unsaturated part of the fatty acid of alcohol or the branched part of the fatty acid or alcohol acts to "disorder" the surfactant hydrophobic chains and induce formation of lamellar phase.

Examples of liquid fatty acids which may be used are oleic acid, isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Examples of alcohols include oleyl alcohol and isostearyl alcohol. Examples of ether derivatives include isosteareth or oleth carboxylic acid; or isosteareth or oleth alcohol.

The structuring agent may be defined as having melting point below about 25° C. centigrade.

Oil/Emollient

One of the principle benefits of the invention is the ability to suspend oil/emollient particles in a lamellar phase composition.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylatelte lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

It should be understood that where the emollient may also function as a structurant, it should not be doubly included such that, for example, if the structurant is 15% oleyl alcohol, no more than 5% oleyl alcohol as "emollient" would be added since the emollient (whether functioning as emollient or structurant) never comprises more than 20%, preferably no more than 15% of the composition.

The emollient/oil is generally used in an amount from about 1 to 20%, preferably 1 to 15% by wt. of the composition. Generally, it should comprise no more than 20% of the composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil$^{(R)}$ from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330-Polyquaternium 39; and Jaguar$^{(R)}$ type conditioners.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm $^{(R)}$ (PEG modified glyceryl cocoate, palmate or tallowate) from Rewo Chemicals; Antil$^{(R)}$ 141 (from Goldschmidt).

Another optional ingredient which may be added are the defloculating polymers such as are taught in U.S. Pat. No. 5,147,576 to Montague, hereby incorporated by reference.

Another ingredient which may be included are exfoliants such as polyoxyethylene beads, walnut sheets and apricot seeds In a second embodiment of the invention, the invention relates to a method of inducing the formation of lamellar phase liquid compositions comprising:

(a) Surfactant system as defined above (i.e., one or more anionics, amphoteric/zwitterionic and optional nonionic); and (b) Emollient/oil as defined above;

which method comprises adding to the composition 0.1 to 20%, preferably 0.1 to 15% by wt. of a structurant as defined above.

In general, the surfactants are mixed uniformly at elevated temperatures (150 to 180° F.) with deionized water. To this are added the auxiliary thickeners, emollient oils, the structurant, the preservatives, and antioxidants. The mixture is mixed to uniformity and then cooled to 90°–95° F. Perfume and other temperatures sensitive ingredients (colors) are added at around 100°–120° F. as it is being cooled. The structurant and the emollient oils can also be added at the low temperatures as it is being cooled.

The invention will now be described in greater detail by way of the following non-limiting examples. The examples are for illustrative purposes only and not intended to limit the invention in any way.

All percentages in the specification and examples are intended to be by weight unless stated otherwise.

EXAMPLES

Compositions I–IX below were prepared as follows:

Surfactants were mixed at 150–180° F. with deionized water followed by addition of auxiliary thickeners, emollient oils, the structurant, preservatives and antioxidants. The mixture was mixed to uniformity and cooled to 90–95° F. Perfumes and sensitives (e.g., colors) were added at about 100–120° F. as it was being cooled. Structurant and emollient oils can also be added at lower temperatures.

Compositions I–IX are set forth below:

| Ingredients | I | II | III | IV | V | VI | VII | VIII | IX |
|---|---|---|---|---|---|---|---|---|---|
| Cocoamido Propyl Betaine | 10 | 8 | 8 | 10 | 10 | 7.5 | 10 | 10 | 0 |
| Sodium Cocoamphoacetate | 0 | 0 | 0 | 0 | 0 | 0 | 0 | 0 | 10 |
| Sodium Cocoyl Isethionate | 5 | 7.5 | 7.5 | 0 | 0 | 0 | 0 | 0 | 5 |
| Alkyl Polyglucoside | 0 | 0 | 0 | 5 | 0 | 0 | 0 | 0 | 0 |
| Laureth-4 Alcohol | 0 | 0 | 0 | 0 | 5 | 0 | 0 | 0 | 0 |
| Sodium Laureth-13 Carboxylate | 0 | 0 | 0 | 0 | 0 | 7.5 | 0 | 0 | 0 |
| Disodium laureth sulfosuccinate | 0 | 0 | 0 | 0 | 0 | 0 | 5 | 0 | 0 |
| Laureth-3 phosphate | 0 | 0 | 0 | 0 | 0 | 0 | 0 | 5 | 0 |
| Ammonium Laureth Sulfate | 5 | 4.5 | 4.5 | 5 | 5 | 5 | 5 | 5 | 5 |
| Dimethicone | 0 | 0 | 5 | 5 | 5 | 5 | 5 | 5 | 5 |
| Castor Oil | 5 | 5 | 0 | 0 | 0 | 0 | 0 | 0 | 0 |
| Glycerine | 1.0 | 1.0 | 1.0 | 1.0 | 1.0 | 1.0 | 1.0 | 1.0 | 1.0 |
| Oleic acid | 0 | 0.0 | 4.5 | 5.0 | 0 | 0 | 0 | 0 | 0 |
| Isostearic acid | 0 | 0 | 0 | 0 | 4.5 | 4.5 | 4.5 | 4.5 | 4.5 |
| Oleyl alcohol | 0 | 5.0 | 0 | 0 | 0 | 0 | 0 | 0 | 0 |
| Propylene glycol isostearate | 4.5 | 0 | 0 | 0 | 0 | 0 | 0 | 0 | 0 |
| PEG-120 Methyl Glucose Dioleate | 0.5 | 0.5 | 0.5 | 0.25 | 0 | 0 | 0 | 0 | 0 |
| Guar Hydroxypropyl-trimonium Chloride | 0.25 | 0.25 | 0.25 | 0.1 | 0.25 | 0.25 | 0.25 | 0.25 | 0.25 |
| Titanium Dioxide | 0.2 | 0.2 | 0.2 | 0.2 | 0.2 | 0.2 | 0.2 | 0.2 | 0.2 |
| EDTA | 0.02 | 0.02 | 0.02 | 0.02 | 0.02 | 0.02 | 0.02 | 0.02 | 0.02 |
| EHDP | 0.02 | 0.02 | 0.02 | 0.02 | 0.02 | 0.02 | 0.02 | 0.02 | 0.02 |
| DDM Hydantoin | 0.2 | 0.2 | 0.2 | 0.02 | 0.02 | 0.02 | 0.02 | 0.02 | 0.02 |
| Fragrance | 1.0 | 1.0 | 0.8 | 1.0 | 0.02 | 0.02 | 0.02 | 0.02 | 0.02 |
| BHT | 0.0075 | 0.0075 | 0.0075 | 0.0075 | 0.0075 | 0.0075 | 0.0075 | 0.0075 | 0.0075 |
| Water | to 100.0 | to 100.0 | to 100.0 | to 100.0 | to 100.0 | to 100.0 | to 100.0 | to 100.0 | to 100.0 |

In each case addition of structurant caused formation of lamellar phase. It should be noted that structurant was used in a variety of surfactant systems, always with the same result, i.e., induction of lamellar phase.

We claim:

1. A method for inducing a lamellar phase in a liquid cleansing composition comprising:
   (a) 5% to 50% by wt. of a surfactant system comprising:
      (i) an anionic surfactant selected from the group consisting of acyl isethionates, alkyl sulfates, alkyl carboxylates, alkyl sulfosuccinates, alkyl phosphates and mixtures thereof; and
      (ii) an amphoteric and/or zwitterionic surfactant selected from the group consisting of amphoacetates, betaines and mixtures thereof; and
   (b) 1 to 20% by wt. emollient, even where said emollient and a structurant defined in (b)(i) and (b)(ii) below are the same; which method comprises adding about 0.1 to 15% by wt. of a structurant selected from the group consisting of:
      (i) $C_8$ to $C_{24}$ unsaturated and/or branched liquid fatty acid selected from the group consisting of oleic acid and isostearic acid; or an ester derivative of said fatty acid selected from the group consisting of propylene glycol isostearate, propylene glycol oleate, glyceryl isostearate, glyceryl oleate, and polyglyceryl diisostearate; and
      (ii) oleyl alcohol or ether thereof;
   wherein said structurant has a melting point below about 25° C.

2. A method according to claim 1, wherein the surfactant system further comprises nonionic surfactant or mixture of nonionic surfactants.

3. A method according to claim 1, wherein the emollient is silicone.

4. A method according to claim 1, wherein the emollient is vegetable oil.

5. A method according to claim 1, wherein the emollient is an ester.

* * * * *